(12) United States Patent
Jo et al.

(10) Patent No.: US 12,121,743 B2
(45) Date of Patent: Oct. 22, 2024

(54) NON-INVASIVE OPTOGENETIC STIMULATION METHOD TO REGULATE GLUCOSE METABOLISM IN THE LIVER AND BROWN ADIPOSE TISSUE

(71) Applicant: Albert Einstein College of Medicine, Bronx, NY (US)

(72) Inventors: Young-Hwan Jo, Cresskill, NJ (US); Jae Hoon Jeong, Elmsford, NY (US); Streamson Chua, Jr., Dobbs Ferry, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 838 days.

(21) Appl. No.: 16/605,360

(22) PCT Filed: Apr. 2, 2018

(86) PCT No.: PCT/US2018/025639
§ 371 (c)(1),
(2) Date: Oct. 15, 2019

(87) PCT Pub. No.: WO2018/194823
PCT Pub. Date: Oct. 25, 2018

(65) Prior Publication Data
US 2020/0046996 A1 Feb. 13, 2020

Related U.S. Application Data

(60) Provisional application No. 62/487,599, filed on Apr. 20, 2017.

(51) Int. Cl.
| | |
|---|---|
| *A61K 48/00* | (2006.01) |
| *A61K 38/17* | (2006.01) |
| *A61N 5/06* | (2006.01) |
| *C12N 7/00* | (2006.01) |
| *C12N 15/63* | (2006.01) |
| *C12N 15/86* | (2006.01) |
| *A01K 67/00* | (2006.01) |

(52) U.S. Cl.
CPC ............ *A61N 5/062* (2013.01); *A61K 38/177* (2013.01); *A61K 48/0058* (2013.01); *A61N 5/0622* (2013.01); *A61N 5/0625* (2013.01); *C12N 7/00* (2013.01); *C12N 15/86* (2013.01); *A61N 2005/0645* (2013.01); *A61N 2005/0651* (2013.01); *A61N 2005/0663* (2013.01); *C12N 2750/14143* (2013.01); *C12N 2750/14171* (2013.01)

(58) Field of Classification Search
CPC .... A61N 5/062; A61N 5/0622; A61N 5/0625; A61K 48/0058; C12N 15/86; C12N 2750/14143; C12N 2750/14171
See application file for complete search history.

(56) References Cited

U.S. PATENT DOCUMENTS

| | | | |
|---|---|---|---|
| 10,080,355 B2 * | 9/2018 | Ryu | .................... A61K 49/0008 |
| 10,974,065 B2 * | 4/2021 | Smith | ................... A61N 5/0622 |
| 2016/0030765 A1 | 2/2016 | Towne et al. | |

FOREIGN PATENT DOCUMENTS

WO 2016/070286 A1 5/2016

OTHER PUBLICATIONS

Jeong et al. Cholinergic neurons in the dorsomedial hypothalamus regulate mouse brown adipose tissue metabolism. Molecular Metabolism 4:483-492, (Year: 2015).*
Wu et al. Activating brown adipose tissue for weight loss and lowering of blood glucose levels: A microPET study using obese and diabetic model mice. PLOS ONE; doi:10.1371/journal.pone.0113742, 14 pages, (Year: 2014).*
Rothermel et al. Transgene expression in target-defined neuron populations mediated by retrograde infection with adeno-associated viral vectors. J. Neuroscience 33:15195-15206, (Year: 2013).*
Lindeberg et al. Transgenic expression of Cre recombinase from the tyrosine hydroxylase locus. Genesis 40:67-73, (Year: 2004).*
Hankir et al. A BAT-centric approach to the treatment of diabetes: Turn on the brain. Cell Metabolism 24:31-40, (Year: 2016).*

* cited by examiner

*Primary Examiner* — Quang Nguyen
(74) *Attorney, Agent, or Firm* — Fox Rothschild LLP

(57) ABSTRACT

Methods and devices are disclosed for non-invasive optogenetic stimulation of autonomic efferent fibers to regulate glucose metabolism in the liver and brown adipose tissue and to treat metabolic disorders.

4 Claims, 7 Drawing Sheets

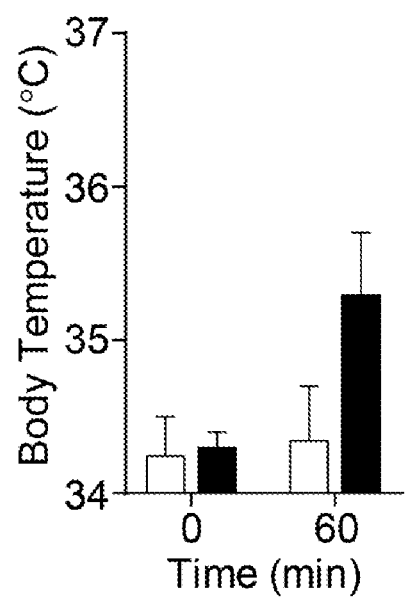 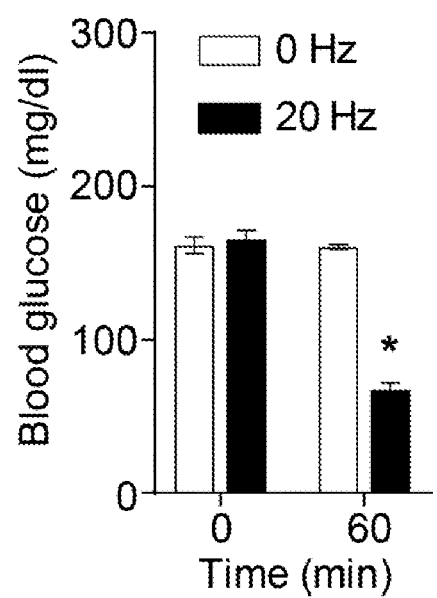
FIG. 4A                    FIG. 4B

NON-INVASIVE OPTOGENETIC STIMULATION METHOD TO REGULATE GLUCOSE METABOLISM IN THE LIVER AND BROWN ADIPOSE TISSUE

CROSS-REFERENCE TO RELATED APPLICATION

This application claims the benefit of U.S. Provisional patent application No. 62/487,599, filed on Apr. 20, 2017, the contents of which is herein incorporated by reference in its entirety.

BACKGROUND OF THE INVENTION

Throughout this application various publications are referred to in parenthesis. Full citations for these references may be found at the end of the specification immediately preceding the claims. The disclosures of these publications are hereby incorporated by reference in their entireties into the subject application to more fully describe the art to which the subject application pertains.

The liver plays a major role in blood glucose homeostasis by maintaining a balance between the uptake and storage of glucose via glycogenesis and the release of glucose via glycogenolysis and gluconeogenesis. This process is highly regulated through neural connections between the liver and the autonomic nervous system. The liver is innervated by both sensory afferent and autonomic efferent nerves. Autonomic efferent innervation of the liver originates mainly in two areas including the intermediolateral cell column of the spinal cord and the dorsal motor nucleus of the vagus. Both of these regions contain preganglionic neurons that innervate liver. Adrenergic receptors for the sympathetic neurotransmitter epinephrine and norepinephrine are present in the liver and cholinergic receptors for the parasympathetic neurotransmitter acetylcholine are involved in control of liver metabolism. The liver consists of parenchymal cells (i.e., hepatocytes) and non-parenchymal cells such as stellate and Kupffer cells. These cells express cholinergic and adrenergic receptors that contribute to diverse liver function. Early pharmacological studies demonstrate that cholinergic and adrenergic receptors on hepatocytes contribute to the regulation of hepatic glucose production in vitro and in vivo.

Interscapular brown adipose tissue (BAT) is the principal site of nonshivering thermogenesis and contains a high density of mitochondria with high amount of uncoupling protein-1 (UCP-1), a protein that allows for the uncoupling of fatty acid oxidation from ATP production to generate heat (1-3). In addition, BAT possesses a great capacity for glucose uptake and metabolism (2, 4). For instance, cold exposure increases glucose uptake by BAT in rodents as well as humans (5, 6). Importantly, both BAT thermogenesis and glucose uptake are highly regulated by the autonomic nervous system (3). Although the function of the parasympathetic nervous system in BAT remains elusive, mice lacking the β-adrenergic receptor are cold intolerant (7) and activation of the β3-adnergic receptor in BAT stimulates glucose uptake (8-10). Therefore, the sympathetic nervous system (SNS) plays an essential role in regulating BAT thermogenesis and glucose utilization (4,11). BAT plays a critical role in regulating glucose hemostasis in rodents and humans (17-19).

Although the autonomic nervous system (ANS) innervates both liver and BAT and regulates glucose metabolism in these organs, studies to date have not examined the effects of "selective" stimulation of sympathetic innervation of BAT mainly due to lack of sufficiently precise experimental approaches. Most studies have examined the effects of systemic administration of adrenergic and cholinergic agonists that regulate not only liver and BAT but also other peripheral organs such as pancreas, heart, and muscle (12-16). As such, altered blood glucose levels following drug administration may well be due to alterations in insulin release from pancreas, altered insulin sensitivity in muscle and liver, hepatic glucose production, and increased BAT activity.

Recent advances in optogenetics have enabled precise control of specific cells or fibers at the millisecond timescale in freely moving animals (25) Optogenetics is the technology that uses visible light to trigger changes in proteins that modulate membrane potentials in neuronal cells through excitatory or inhibitory membrane currents. For instance, channelrhodopsin 2 (ChR2) is a transmembrane ion channel found in green algae that becomes permeable to cations in the presence of blue light. ChR2 can be used in neurons as ion channels are a main contributor in electrical signal transduction in the nervous system. This ability to modulate neuronal cells has proven instrumental in preclinical studies and holds enormous potential for the treatment of diseases such as Parkinson's disease, epilepsy, and depression.

Although the ability of optogenetics to modulate neuronal activity has proven helpful in preclinical studies and has the potential for the treatment of neurological disorders, the current techniques are too invasive for practical clinical application in humans. In current implementations, optical fibers are surgically implanted in organs to deliver light. Moreover, optical fibers need to be connected to an expensive and relatively big laser or a LED as the light source. These technical limitations make it difficult to develop clinical devices. The present invention addresses the need for methods and devices for non-invasive optogenetic therapy.

SUMMARY OF THE INVENTION

The invention provides methods and devices for non-invasive optogenetic therapy.

Non-invasive optogenetic methods are provided for modulating the activity of metabolic organs, such as liver and BAT, in a subject, where the methods comprise applying light through the skin of the subject to activate a transmembrane ion channel channelrhodopsin virally-induced in autonomic efferent nerve fibers innervating the organ, where the light is applied in a wavelength, amount and duration effective to modulate activity of the organ in a subject.

The invention also provides devices for non-invasive optogenetic stimulation, where the devices comprise one or more surface-mounted-device light-emitting device (SMD-LED) modules, a Transistor-Transistor Logic (TTL) pulse generator, and a power supply, wherein the devices are configured to be mounted on the skin of a subject.

BRIEF DESCRIPTION OF THE DRAWINGS

FIG. 4A-4B. Channelrhodopsin expression in sympathetic efferent nerve fibers using an AAV having a tyrosine hydroxylase (Th) promoter. An AAV vector carrying ChR2 expression cassette under control of the Th promoter was injected in BAT of wild-type mice. Graphs showing effects of optogenetic stimulation of ChR2-expressing fibers on body temperature (A) and blood glucose levels (B) in wild-type mice injected with AAV8-Th promoter-ChR2-eYFP (n=2 mice).

DETAILED DESCRIPTION OF THE INVENTION

Figure 1:
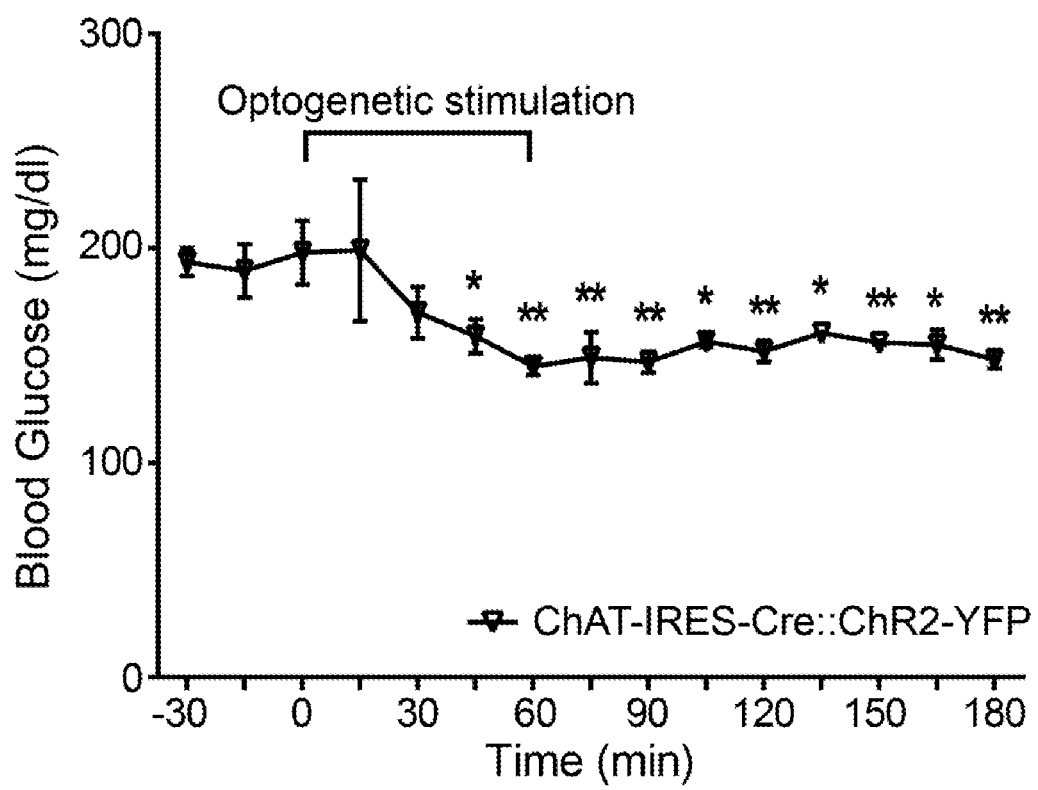
FIG. 1. Conventional optogenetic stimulation of autonomic efferent fibers in the liver reduces blood glucose levels. An optogenetic fiber was placed directly in the liver parenchyma of ChAT-IRES-Cre::ChR2-YFP mice. Optogenetic stimulation of cholinergic fibers at 20 Hz for 1 hr strongly reduced blood glucose levels.

The invention provides a non-invasive optogenetic method for modulating the activity of a metabolic organ in a subject, the method comprising applying light through the skin of the subject to activate a transmembrane ion channel channelrhodopsin virally-induced in autonomic efferent nerve fibers innervating the organ, where the light is applied in a wavelength, amount and duration effective to modulate activity of the organ in a subject.

The organ can be, for example, liver or brown adipose tissue.

The channelrhodopsin can be, for example, channelrhodopsin2 (ChR2), and the light is blue light. The blue light can have a wavelength of ~450 to 475 nm. In another embodiment, the channelrhodopsin can be a red-shifted variant of channelrhodopsin, and the light is red light. The red light can have a wavelength of ~590 to 630 nm.

For the present invention, light-activated transmembrane ion channel proteins need to be expressed in target neurons. This can be accomplished, for example, using adeno-associated viruses (AAV) for expression of a transmembrane ion channel channelrhodopsin (e.g., ChR-2 or a red-shifted variant of channelrhodopsin (24)).

Adeno-associated virus (AAV) is a non-enveloped, single-stranded, small DNA virus of the Parvovirus family. As infection with wild-type AAV is not associated with any known illness, AAV has been used for long-term, stable gene expression in neurons in mammals, with little or no toxicity. The naturally occurring AAV integrate its genome into the host chromosome, but the deletion of the rep genes (that are required for the AAV life cycle) from the vector form of AAV lead to the loss of this integration. In other words, most AAV genomes exist as non-integrated episomes as single viral genomes. This feature is particularly important because the random integration of the therapeutic vector genome within the host DNA can lead to malignancy. No AAV vector-induced malignancy has been reported in clinical gene transfer studies.

Gene transfer studies using AAV have shown significant progress at the level of animal models and clinical trials and have been noteworthy with respect to the safety of AAV vectors (e.g., 23). There are a number of clinical trials using AAV vectors (as of 2011, there are more than 20 clinical trials). Among them, three groups undertook gene therapy trials for the retinal degenerative disorder Leber's congenital amaurosis (early-onset blindness) (NCT00643747, NCT00516477, and NCT00481546). They found that immune responses to AAV serotype 2 (AAV2) and transgene product were minimal and more than 25 subjects injected with the AAV vector showed some improvements in visual function that persisted for periods of over 3 years. Moreover, a recent clinical trial of RetroSence Therapeutics (NCT02556736; Phase I/II) uses the AAV2 that encodes channelrhodopsin-2 (ChR2) for retinitis pigmentosa.

Adeno-associated virus (AAV) is replication-defective and cannot cross synapses without replication. In general, AAV particles are taken up by axon terminals of the neurons projecting to the infected organ and then AAV is transported either anterogradely or retrogradely to neuronal cell bodies. Importantly, the infection and direction are determined mainly by the serotypes of AAV. AAV serotypes 1, 8, and 9 are anterogradely and retrogradely transported (20). AAV6 is also retrogradely transported to cell bodies.

Importantly, the natural promoters of AAV can be replaced with other promoters. This means that one can use AAV vectors that have the choline acetyltransferase (ChAT) promoter for the parasympathetic cholinergic efferents and the tyrosine hydroxylase (Th) promoter for the sympathetic adrenergic efferents. For example, an AAV vector carrying ChR2 expression cassette under control of the Th promoter (21, 22) can be used. The presence of the Th promoter will drive expression of ChR2 exclusively in catecholaminergic neurons (see FIG. 4).

In one embodiment, the channelrhodopsin is induced in parasympathetic cholinergic efferent nerve fibers using an adeno-associated virus (AAV) having a choline acetyltransferase (ChAT) promoter. In another embodiment, the channelrhodopsin is induced in sympathetic adrenergic efferent nerve fibers using an adeno-associated virus (AAV) having a tyrosine hydroxylase (Th) promoter.

A similar approach has been used in clinical trials of AAV delivery to liver (e.g. AAV vector with a liver-specific promoter consisting of the human al-antitrypsin promoter with the apolipoprotein enhancer and elements of the hepatic control region; NCT00076557, NCT00515710, and NCT00979238). Interestingly, AAV vector was administered through intramuscular, hepatic, and intravenous routes in these clinical trials. In other words, direct injection of AAV to target organs is not absolutely necessary.

Viral injections can be made directly into peripheral target organs, such as liver and brown adipose tissue.

The activation of human brown adipose tissue (BAT) represents an opportunity to increase energy expenditure and weight loss alongside improved lipid and glucose homeostasis (11). Accumulated evidence has suggested that sympathetic innervation contributes to the regulation of BAT activity (4,11). To selectively stimulate sympathetic efferent fibers of BAT, ChR2 can be expressed in sympathetic efferent fibers of BAT by directly injecting a retrograde AAV encoding the ChR2 transgene into BAT.

The penetration depth of light into tissue depends on several factors including light wavelength, wattage, spot size, etc. In general, red light penetrates the skin to a depth of about 8 to 10 mm. Recently, a red-shifted variant of channelrhodopsin that is activated with orange to red light (~590 to 630 nm) has been reported (24). They show that red light can penetrate the mouse skin and even the skull and then activate this newly-developed red-shifted channelrhodopsin in rodents.

Non-invasive optogenetic stimulation of autonomic efferent nerve fibers to the liver can be used to regulate hepatic glucose metabolism. Activation of cholinergic parasympathetic efferent nerve fibers to the liver can be used to reduce blood glucose levels in a subject. Activation of catecholaminergic sympathetic efferent nerve fibers to the liver can be used to increase blood glucose levels in the subject. The subject can have type 2 diabetes or pre-diabetes or hyperglycemia.

Non-invasive optogenetic stimulation of autonomic efferent nerve fibers to brown adipose tissue (BAT) can be used to regulate one or more of BAT thermogenesis, core body temperature and blood glucose levels. Activation of catecholaminergic sympathetic efferent nerve fibers to BAT can be used to do one or more of increasing BAT thermogenesis and core body temperature, and decreasing blood glucose levels in a subject. The subject can have type 2 diabetes, pre-diabetes or hyperglycemia.

In the non-invasive optogenetic stimulation method, the light can be applied to the subject using a device mounted on the skin of the subject over the organ of interest, where the device comprises one or more surface-mounted-device light-emitting device (SMD-LED) modules, a Transistor-Transistor Logic (TTL) pulse generator, and a power supply.

The light applied to the subject can have an intensity of, for example, 180 lumens. The light can be presented to the subject, for example, in 20 msec pulses at a frequency of 20 Hz. Pulses of light can be applied to the subject in, for example, on/off cycles of 1-3 sec duration. The light can be applied to the subject for a duration, for example, of 30 minutes to three hours.

The invention also provides a device for non-invasive optogenetic stimulation, where the device comprises:
one or more surface-mounted-device light-emitting device (SMD-LED) modules,
a Transistor-Transistor Logic (TTL) pulse generator, and
a power supply,
where the device is configured to be mounted on the skin of a subject.

The light-emitting device can comprise one or more SMD-light-emitting diodes. Each module of the device can be, for example, about 2 mm by 2 mm square. The TTL pulse generator can, for example, be incorporated in a pulse generator circuit board. The TTL pulses can, for example, use 5 volt TTL logic levels. Preferably, the device uses no more than about three watts of power.

The SMD-LED device can, for example, emit blue light or red light. The light can have an intensity of, for example, about 180 lumens. The light can be generated, for example, in 20 msec pulses at a frequency of 20 Hz. Pulses of light can be generated in, for example, on/off cycles of 1-3 sec duration.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction and Overview

A non-invasive optogenetic stimulation method was developed to regulate glucose metabolism in the liver and brown adipose tissue (BAT) in freely moving animals. It is known that blue light (453 nm) readily penetrates human skin. We took advantage of this property to develop a non-invasive optogenetic stimulation method that permits direct stimulation of channelrhodopsin-expressing autonomic efferent fibers to the liver and BAT. Surface-mounted-device light-emitting device (SMD-LED) modules were used as a light source. The SMD-LED can be mounted onto and soldered onto a tiny circuit board and is quite small. Importantly, the SMD-LED gives off almost no heat and has low voltage and current requirements. This physical feature of the SMD-LED allows it to be applied directly to the abdominal skin since the skin is not irritated by heat during light stimulation. Individual modules are controlled by 5 V TTL logic levels. This innovative method can be easily applied to humans since it does not require surgery to implant optogenetic devices into target organs.

In our studies of mice expressing light-activated stimulatory proteins in cholinergic and catecholaminergic preganglionic neurons, 3 W SMD-LED modules controlled by TTL logic levels were applied directly to abdominal skin below the ribcage of mice. This non-invasive optogenetic stimulation method significantly altered plasma blood glucose levels in mice. Specifically, non-invasive optogenetic activation of sympathetic adrenergic fibers in the liver increased, whereas stimulation of parasympathetic cholinergic fibers decreased blood glucose levels. Activation of catecholaminergic sympathetic efferent fibers to BAT increased BAT thermogenesis and core temperature, and decreased blood glucose levels. Therefore, the present non-invasive optogenetic stimulation method will open up new therapeutic strategies to control blood glucose levels in people with diabetes in particular.

Liver Parenchyma Contains Autonomic Efferent Fibers

The distribution of autonomic nerve fibers was examined in the liver parenchyma. To this end, two strains of mice were generated: the tyrosine hydroxylase (Th)-Cre::tdTomato strain to identify sympathetic catecholaminergic fibers, and the choline acetyltransferase (ChAT)-IRES-Cre::tdTomato strain to examine the distribution of hepatic parasympathetic cholinergic efferent fibers. Both parasympathetic and sympathetic efferent fibers were clearly observed throughout the liver parenchyma. Most Th- and ChATpositive fibers appear to be adjacent to the sinusoids and possibly hepatocytes. Therefore, both animal models are ideal for studying the functional roles of autonomic neural circuits of the liver.

Conventional Invasive Optogenetic Stimulation of Autonomic Efferent Fibers in the Liver The liver expresses adrenergic and cholinergic receptors that are activated by neurotransmitters released from autonomic sympathetic and parasympathetic efferent fibers. To examine the functions of the parasympathetic cholinergic fibers, the ChAT-IRES-Cre::ChR2-YFP mice were generated. Under isoflurane anesthesia, parasympathetic efferent fibers were illuminated by directly placing an optogenetic fiber coupled with a laser or an LED in the liver parenchyma. Bursts of light pulses were applied for 1 second followed by a 1 second break that repeated continuously for 1 hour (FIG. 1). This optogenetic stimulation readily reduced blood glucose levels, consistent with parasympathetic activation. Although these findings are very promising, surgical implantation of an optic fiber into the liver was needed to selectively stimulate autonomic efferent fibers under isoflurane anesthesia. Moreover, one cannot monitor blood glucose levels in freely moving animals with this invasive optogenetic stimulation method.

Development of a Non-Invasive Optogenetic Stimulation Method

Figure 2A:
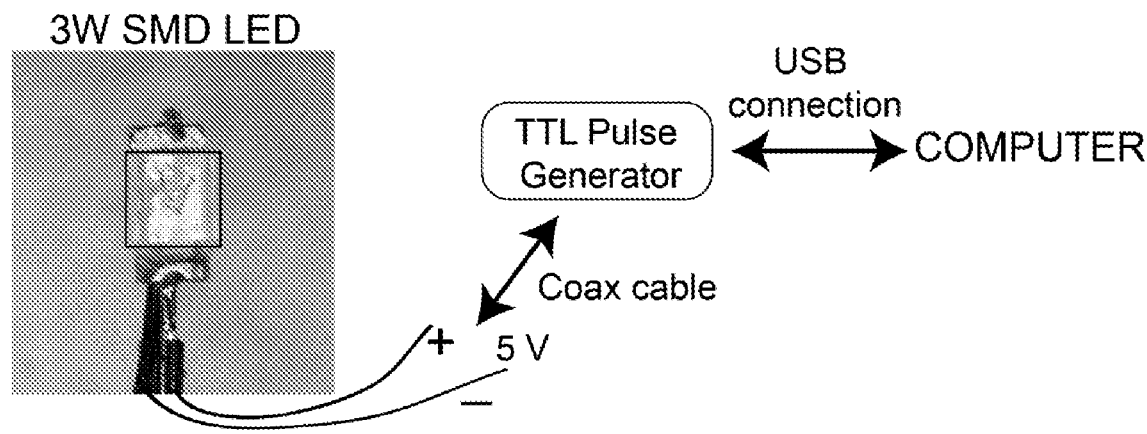
FIG. 2A-2E. Non-invasive optogenetic stimulation method. (A) A small (2×2 mm box) three watt SMD blue LED was connected to a TTL pulse generator controlled by a computer. (B) Images showing placement of SMD LEDs on abdominal skin of mice. (C) Illustration showing optogenetic stimulation protocol. ChAT-Cre::ChR2 (D) and Th-Cre::ChR2 (E) mice were generated to study the physiological functions of the autonomic nervous system. Non-invasive optogenetic stimulation of cholinergic efferent fibers reduced, whereas activation of catecholaminergic efferent fibers increased blood glucose levels, supporting the use of this non-invasive method as being as efficient as the invasive method (n=6 and 5 mice, respectively). Efferent fibers were stimulated at 20 Hz for 1 hr. *p<0.05, p<0.01, *p<0.001.
Figure 2B:
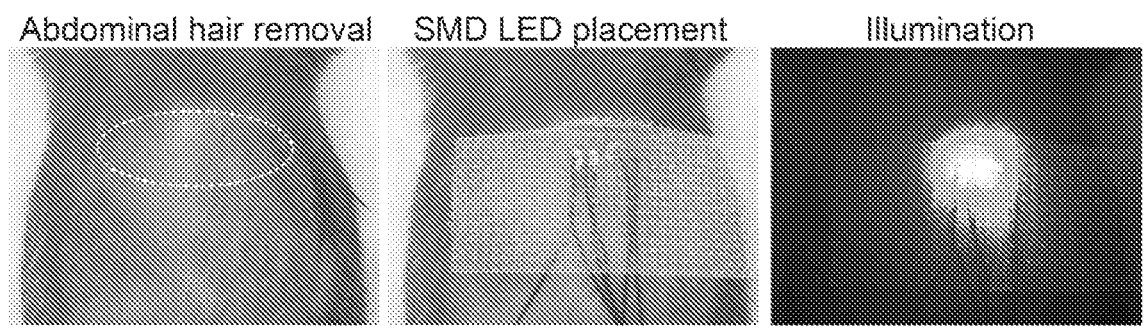
Figure 2C:
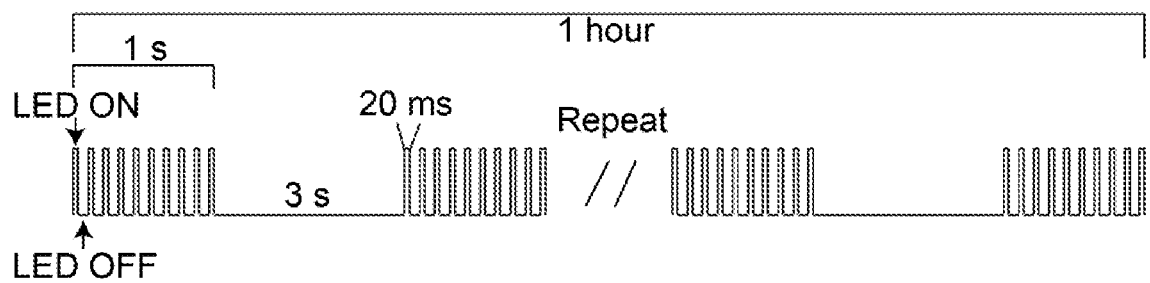
Figure 2D:
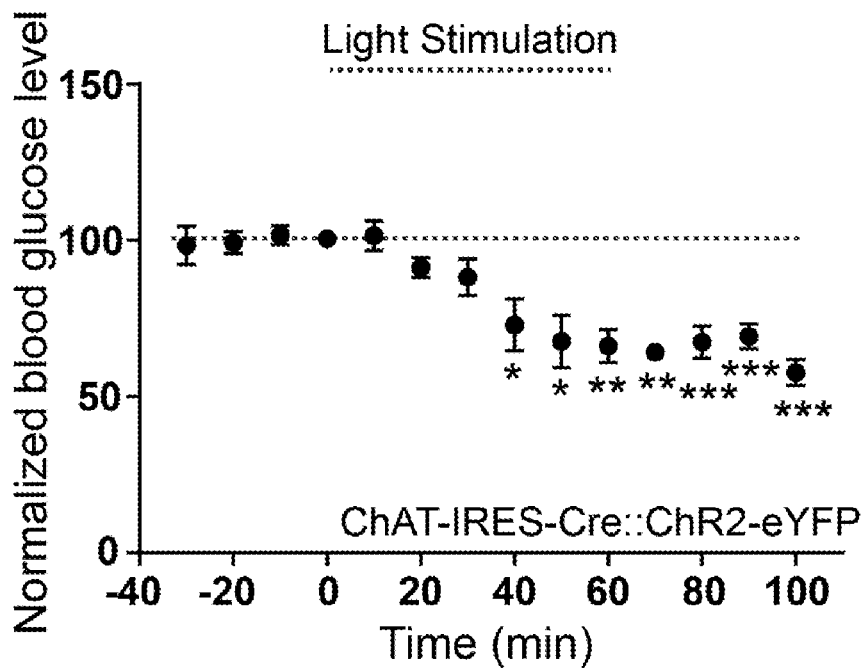
Figure 2E:
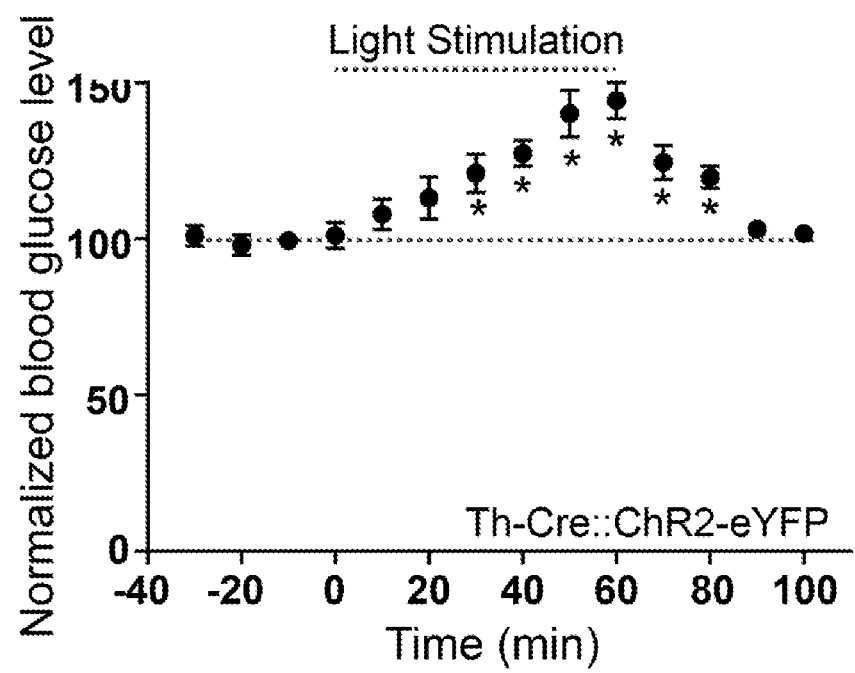

To overcome existing limitations, a non-invasive optogenetic stimulation method was developed. Small (2 mm×2 mm) 3 W SMD-LED (180 lumen of blue light) modules were directly applied to the abdominal skin just above the liver (FIG. 2). Individual modules were controlled by 5 V TTL logic levels that were generated by a TTL pulse generator (Doric Lenses). The pulse train parameters were controlled via an interface of open source OTPG4 controller software (Doric lenses) (FIG. 2A). Under these experimental conditions, the abdominal skin of ChAT-Cre::ChR2 and Th-Cre::ChR2 animals overlying the liver parenchyma was illuminated without surgical implantation of optic fibers into the liver (FIG. 2B). Bursts of light pulses at 20 Hz were applied for 1 s followed by a 1 s break that repeated continuously for 1 hr (FIG. 2C). This non-invasive optogenetic stimulation of parasympathetic efferent fibers effectively decreased blood glucose levels (FIG. 2D). Additionally, optical stimulation of sympathetic efferent fibers elevated blood glucose levels. Hence, results from these studies support the fact that blue light not only penetrates the skin but also is sufficient to stimulate channelrhodopsin-expressing autonomic efferent fibers to the liver.

Target Organ-Specific Expression of Light-Activated Proteins

The method can use Cre-inducible retrograde AAV (i.e., AAV6, 8, and 9) that encodes ChR2. Importantly, the natural promoters of AAV can be replaced with promoters from other viruses or host cells. This means that one can use AAV vectors that have the choline acetyltransferase (ChAT) promoter for the parasympathetic cholinergic efferents and the tyrosine hydroxylase (Th) promoter for the sympathetic adrenergic efferents (e.g. FIG. 4). In this case, one does not need Cre-expressing neurons to induce expression of ChR2 in autonomic efferent fibers.

Direct Activation of Sympathetic Efferent Fibers of BAT Increases BAT Activity

Figure 3A:
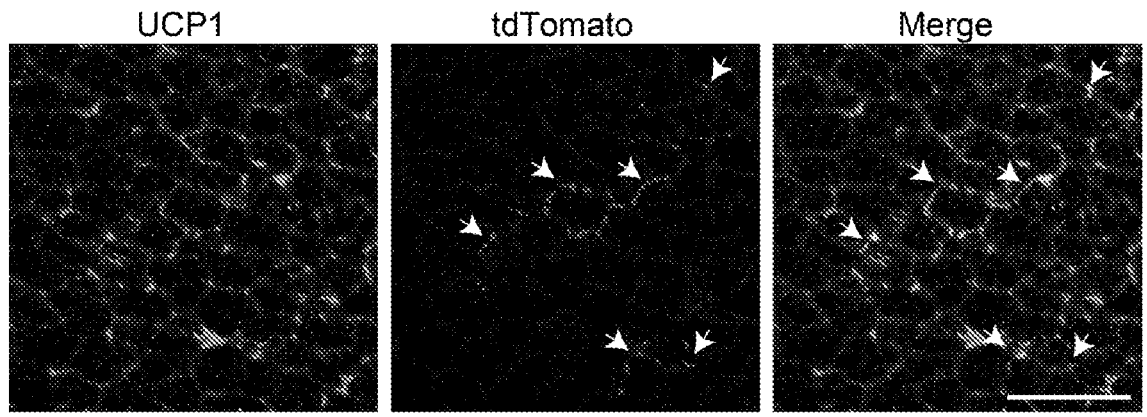
FIG. 3A-3G. Selective activation of sympathetic efferent fibers of BAT. (A) Expression of Th-positive fibers (arrow heads) in BAT of Th-Cre::tdTomato mice. 50 µm calibration bar. (B) Optogenetic stimulation of sympathetic efferents of BAT of Th-Cre::ChR2 mice increased BAT thermogenesis (n=7 mice). Open circle, core temperature and gray square, BAT temperature (C) Expression of ChR2 exclusively in sympathetic efferents innervating BAT via injection of retrograde viral vectors. Th-Cre mice injected with retrograde ChR2. Optogenetic stimulation increased BAT metabolism (n=7 mice). (D) Injecting a ß3 receptor antagonist blocked the effect (n=7 mice). (E) Images showing the novel non-invasive optogenetic stimulation method. Hair on the neck and shoulders was removed and then two SMD LED modules per each side were placed directly on the skin. The skin was illuminated with blue light. (F) Increased plasma norepinephrine (NE) levels during stimulation of sympathetic efferent fibers with the method (n=6 mice). (G) Pooled data showing changes in body temperature and blood glucose levels before, during, and after non-invasive optogenetic stimulation of sympathetic efferent fibers (n=6 mice). ***p<0.001 (unpaired t-test)*p<0.05, p<0.01, *p<0.001, unpaired t-test.
Figure 3B:
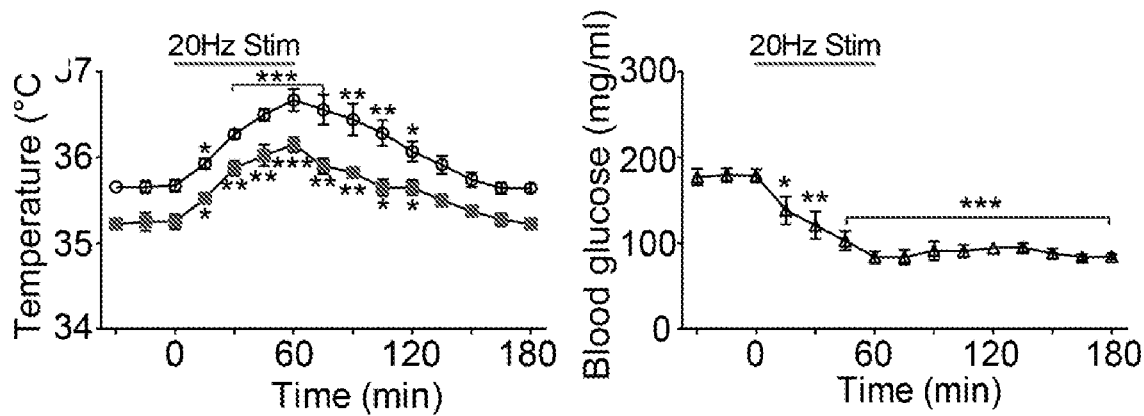

Th-Cre::tdTomato mice were used to examine BAT sympathetic efferent fibers. Immunohistochemical staining showed tdTomato-positive fibers in BAT, indicating that BAT receives catecholaminergic innervation (FIG. 3A). Next Th-Cre::ChR2 mice were generated to optogenetically stimulate sympathetic efferent fibers of BAT. An optic fiber was surgically placed just underneath the BAT pad and sympathetic efferent fibers were optogenetically stimulated at 20 Hz for 1 hr. This optogenetic stimulation readily elevated body core temperature that was associated with reduced blood glucose levels (FIG. 3B, n=7). These results support the interpretation that optogenetic stimulation of sympathetic efferent fibers of BAT enhances BAT metabolism.

Figure 3C:
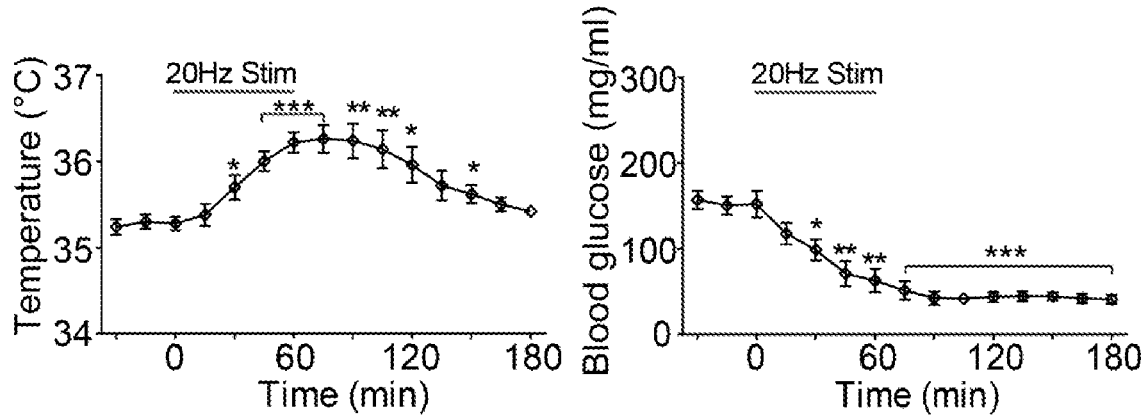
Figure 3D:
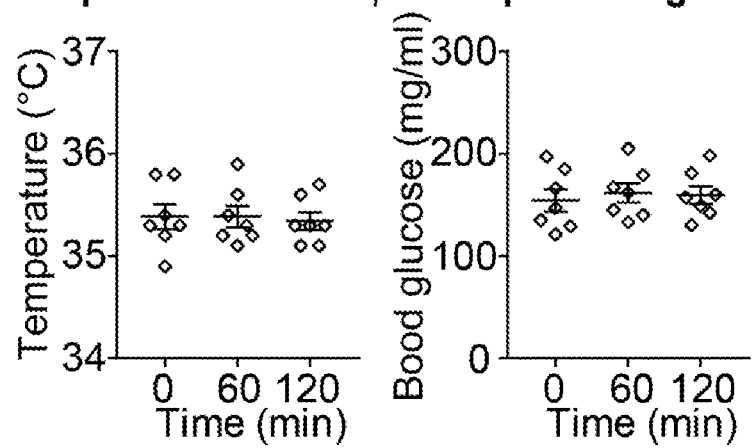

To express ChR2 in sympathetic efferent fibers exclusively innervating BAT, replication-incompetent retrograde herpes simplex virus (HSV) encoding the Cre-inducible ChR2 transgene was bilaterally injected into BAT of Th-Cre mice. At four weeks post viral injection, sympathetic efferents of BAT were optogenetically stimulated, resulting in increased BAT thermogenesis (FIG. 3C). Increased BAT thermogenesis was due to activation of β3-adrenergic receptors in BAT as injection of the β3-adrenergic receptor antagonist (SR59230A) completely abolished the effect of optogenetic stimulation (FIG. 3D). These experiments provide direct evidence for retrograde expression of ChR2 in sympathetic efferent fibers that exclusively innervate BAT.

Non-Invasive Optogenetic Stimulation of Sympathetic Innervation of BAT

Figure 3E:
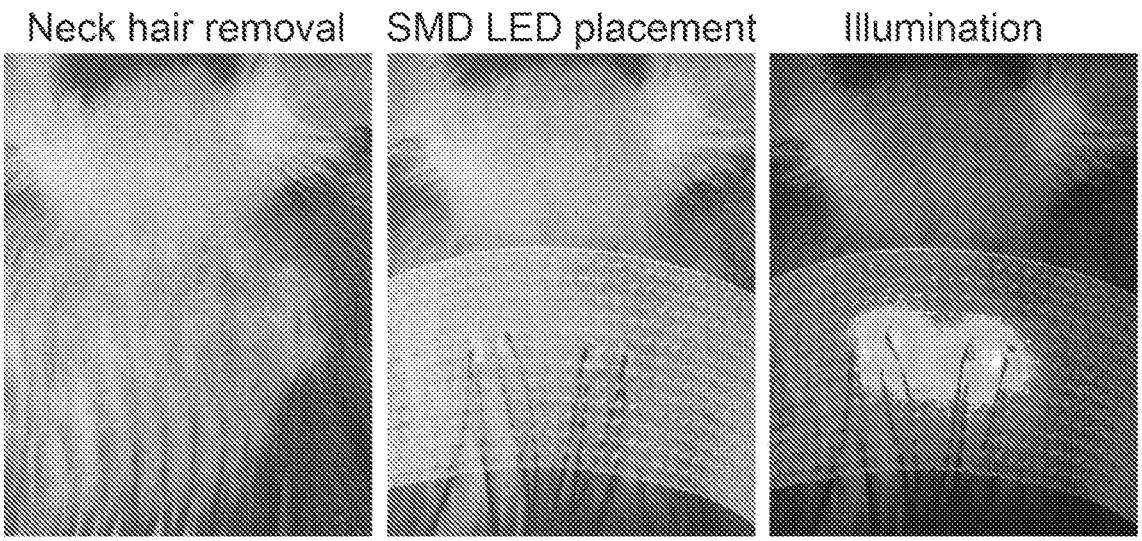
Figure 3F:
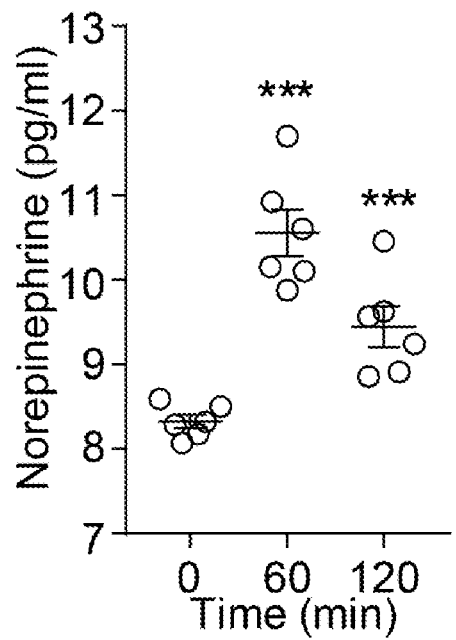

It was then examined whether non-invasive optogenetic stimulation is also able to stimulate sympathetic efferent fibers, resulting in norepinephrine (NE) release. SMD-LED modules were directly placed on the skin of the neck and shoulders (FIG. 3E). This novel non-invasive method was as efficient as the invasive method in that non-invasive optogenetic stimulation significantly increased plasma NE levels, indicating that this non-invasive optogenetic stimulation activates sympathetic efferent fibers of BAT, leading to NE release.

Figure 3G:
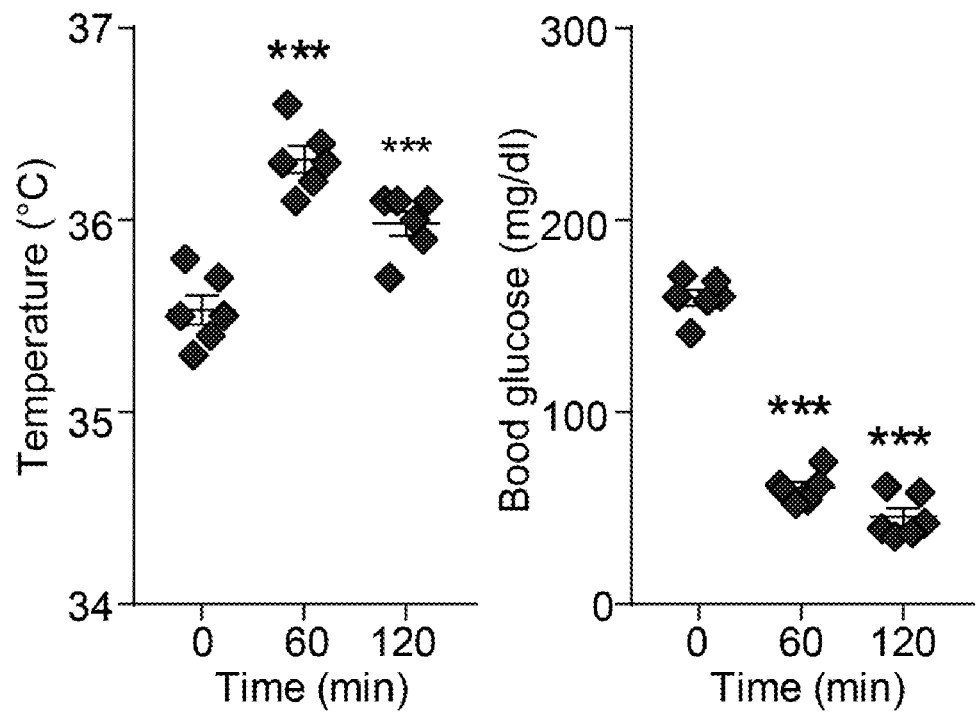

ChR2-expressing sympathetic nerves of BAT were illuminated with bursts of light pulses for 1 hr. Likewise, this non-invasive optogenetic stimulation method was sufficient to raise body temperature and glucose uptake by BAT (FIG. 3G). Therefore, our results support the interpretation that both conventional and non-invasive optogenetic stimulation methods have the capability to stimulate sympathetic nerves of BAT, resulting in nonshivering thermogenic responses and glucose uptake by BAT.

CONCLUSIONS

This invention has several advantages over current optogenetic methods. 1) Since the method is completely non-invasive, it does not need a surgery to implant optogenetic devices into target organs. 2) Since the SMD-LEDs are quite small and can be mounted directly on a circuit board, it is relatively easy to make a small device that can be applied directly to the skin. 3) Since the SMD-LEDs do not produce heat, they are safe to use in animals and humans.

This invention is designed to control blood glucose levels and other metabolic functions in freely moving animals without surgical implantation of optogenetic devices. The non-invasive optogenetic stimulation method will enable new therapeutic strategies to control blood glucose levels in people with diabetes.

REFERENCES

1. Peirce, V., Carobbio, S. & Vidal-Puig, A. The different shades of fat. *Nature* 510, 76-83 (2014).

2. Hankir, M. K., Cowley, M. A. & Fenske, W. K. A BAT-Centric Approach to the Treatment of Diabetes: Turn on the Brain. *Cell Metab*, doi:10.1016/j.cmet.2016.05.003 (2016).
3. Cannon, B. & Nedergaard, J. Brown adipose tissue: function and physiological significance. *Physiol Rev* 84, 277-359 (2004).
4. Townsend, K. L. & Tseng, Y. H. Brown fat fuel utilization and thermogenesis. *Trends Endocrinol Metab* 25, 168-177 (2014).
5. Orava, J. et al. Different metabolic responses of human brown adipose tissue to activation by cold and insulin. *Cell Metab* 14, 272-279 (2011).
6. Nikami, H., Shimizu, Y., Endoh, D., Yano, H. & Saito, M. Cold exposure increases glucose utilization and glucose transporter expression in brown adipose tissue. *Biochem Biophys Res Commun* 185, 1078-1082 (1992).
7. Bachman, E. S. et al. betaAR signaling required for diet-induced thermogenesis and obesity resistance. *Science* 297, 843-845 (2002).
8. Olsen, J. M. et al. Glucose uptake in brown fat cells is dependent on mTOR complex 2-promoted GLUT1 translocation. *J Cell Biol* 207, 365-374 (2014).
9. Dallner, O. S., Chernogubova, E., Brolinson, K. A. & Bengtsson, T. Beta3-adrenergic receptors stimulate glucose uptake in brown adipocytes by two mechanisms independently of glucose transporter4 translocation. *Endocrinology* 147, 5730-5739 (2006).
10. Chernogubova, E., Cannon, B. & Bengtsson, T. Norepinephrine increases glucose transport in brown adipocytes via beta3-adrenoceptors through a cAMP, PKA, and PI3-kinase-dependent pathway stimulating conventional and novel PKCs. *Endocrinology* 145, 269-280 (2004).
11. Whittle, A. J., Lopez, M. & Vidal-Puig, A. Using brown adipose tissue to treat obesity—the central issue. *Trends Mol Med* 17, 405-411 (2011).
12. Boyle, P. J., Liggett, S. B., Shah, S. D. & Cryer, P. E. Direct muscarinic cholinergic inhibition of hepatic glucose production in humans. *The Journal of clinical investigation* 82, 445-449 (1988).
13. Chu, C. A. et al. The direct effects of catecholamines on hepatic glucose production occur via alpha(1)- and beta(2)-receptors in the dog. American journal of physiology. *Endocrinology and Metabolism* 279, E463-473 (2000).
14. Ehlert, F. J., Ostrom, R. S. & Sawyer, G. W. Subtypes of the muscarinic receptor in smooth muscle. *Life Sci* 61, 1729-1740 (1997).
15. Duttaroy, A. et al. Muscarinic stimulation of pancreatic insulin and glucagon release is abolished in m3 muscarinic acetylcholine receptor-deficient mice. *Diabetes* 53, 1714-1720 (2004).
16. Fields, J. Z., Roeske, W. R., Morkin, E. & Yamamura, H. I. Cardiac muscarinic cholinergic receptors. Biochemical identification and characterization. *J Biol Chem* 253, 3251-3258 (1978).
17. Peirce, V. & Vidal-Puig, A. Regulation of glucose homoeostasis by brown adipose tissue. *Lancet Diabetes Endocrinol* 1, 353-360 (2013).
18. Lee, P. et al. Brown Adipose Tissue Exhibits a Glucose-Responsive Thermogenic Biorhythm in Humans. *Cell Metab* 23, 602-609 (2016).
19. Stanford, K. I. et al. Brown adipose tissue regulates glucose homeostasis and insulin sensitivity. *J Clin Invest* 123, 215-223 (2013).
20. Castle, M. J., Gershenson, Z. T., Giles, A. R., Holzbaur, E. L. & Wolfe, J. H. Adeno-associated virus serotypes 1, 8, and 9 share conserved mechanisms for anterograde and retrograde axonal transport. *Hum Gene Ther* 25, 705-720 (2014).
21. Oh, M. S., Hong, S. J., Huh, Y. & Kim, K. S. Expression of transgenes in midbrain dopamine neurons using the tyrosine hydroxylase promoter. *Gene Ther* 16, 437-440 (2009).
22. Rolland, A. S., Kareva, T., Kholodilov, N. & Burke, R. E. A quantitative evaluation of a 2.5-kb rat tyrosine hydroxylase promoter to target expression in ventral mesencephalic dopamine neurons in vivo. *Neuroscience* 346, 126-134 (2017).
23. Mingozzi, F. & High, K. A. Therapeutic in vivo gene transfer for genetic disease using AAV: progress and challenges. *Nature Reviews Genetics* 12, 341-355 (2011).
24. Lin, J. Y., Knutsen, P. M., Muller, A., Kleinfeld, D., Tsien, R. Y. ReaChR: a red-shifted variant of channelrhodopsin enables deep transcranial optogenetic excitation. Nat Neurosci. 16(10):1499-508 (2013), Epub 2013 Sep. 1.
25. Deisseroth, K. and Hegemann, P. The form and function of channelrhodopsin. Science. 2017 Sep. 15; 357 (6356).

What is claimed is:

1. A non-invasive optogenetic method for reducing a blood glucose level in a subject in need thereof, the method comprising:
   injecting into a brown adipose tissue (BAT) of the subject an adeno-associated virus vector having a nucleic acid sequence encoding a transmembrane ion channel channelrhodopsin that is operably linked to a tyrosine hydroxylase (Th) promoter, wherein the transmembrane ion channel channelrhodopsin is activated by blue light having a wavelength of from 450 nm to 475 nm;
   attaching one or more light-emitting modules of a light-emitting device directly above the skin of the subject that is adjacent to the brown adipose tissue, wherein the one or more light-emitting modules have no contact with a subcutaneous tissue under the skin adjacent to the brown adipose tissue; and
   applying the blue light, generated from the light-emitting device, through the skin adjacent to the brown adipose tissue of the subject to activate the transmembrane ion channel channelrhodopsin in sympathetic adrenergic efferent nerve fibers in the brown adipose tissue and to reduce the blood glucose level in the subject, wherein the blue light at an intensity of 180 lumens is applied as a stimulation comprising a burst of 20 millisecond light pulses at 20 Hz for 1 second followed by a 3 second break, and wherein the stimulation is repeated for one hour.

2. The method of claim 1, wherein activation of the transmembrane ion channel channelrhodopsin in the sympathetic adrenergic efferent nerve fibers further increasing BAT thermogenesis, core body temperature, or both.

3. The method of claim 2, wherein the subject has type 2 diabetes, pre-diabetes or hyperglycemia.

4. The method of claim 1, wherein the light-emitting device comprises a Transistor-Transistor Logic (TTL) pulse generator and a power supply.

* * * * *